(12) United States Patent
    Pompa

(10) Patent No.: US 9,594,034 B1
(45) Date of Patent: Mar. 14, 2017

(54) OXFORD STYLE SAMPLE CUP

(71) Applicant: Premier Lab Supply Inc., Port St. Lucie, FL (US)

(72) Inventor: Donato Pompa, Port St Lucie, FL (US)

(73) Assignee: Premier Lab Supply Inc., Port St. Lucie, FL (US)

( * ) Notice: Subject to any disclaimer, the term of this patent is extended or adjusted under 35 U.S.C. 154(b) by 0 days.

(21) Appl. No.: 14/871,266

(22) Filed: Sep. 30, 2015

(51) Int. Cl.
  *G01N 23/22* (2006.01)
  *G01N 23/223* (2006.01)

(52) U.S. Cl.
  CPC ....... *G01N 23/2204* (2013.01); *G01N 23/223* (2013.01)

(58) Field of Classification Search
  None
  See application file for complete search history.

(56) References Cited

U.S. PATENT DOCUMENTS

| | | | | |
|---|---|---|---|---|
| 6,428,751 B1* | 8/2002 | Solazzi | ................... | B01L 3/508 250/428 |
| 6,603,544 B1* | 8/2003 | Eckert | .................. | G01N 23/223 356/244 |
| 6,955,099 B2* | 10/2005 | Goodin | .............. | A61B 10/0045 73/864.51 |
| 7,535,989 B2* | 5/2009 | Russell | ................ | G01N 23/223 378/44 |
| 7,729,471 B2* | 6/2010 | Burdett, Jr. | ........ | G01N 23/2204 378/204 |
| 7,981,380 B2* | 7/2011 | Solazzi | ................... | B01L 3/508 422/400 |
| 2011/0024434 A1* | 2/2011 | Pompa | ..................... | B01L 9/06 220/600 |

* cited by examiner

*Primary Examiner* — Jack Berman
(74) *Attorney, Agent, or Firm* — Joseph Beckman

(57) ABSTRACT

This invention relates to the design and construction of a novel sample cup including an integral venting cap for use in XRF Spectroscopy.

8 Claims, 3 Drawing Sheets

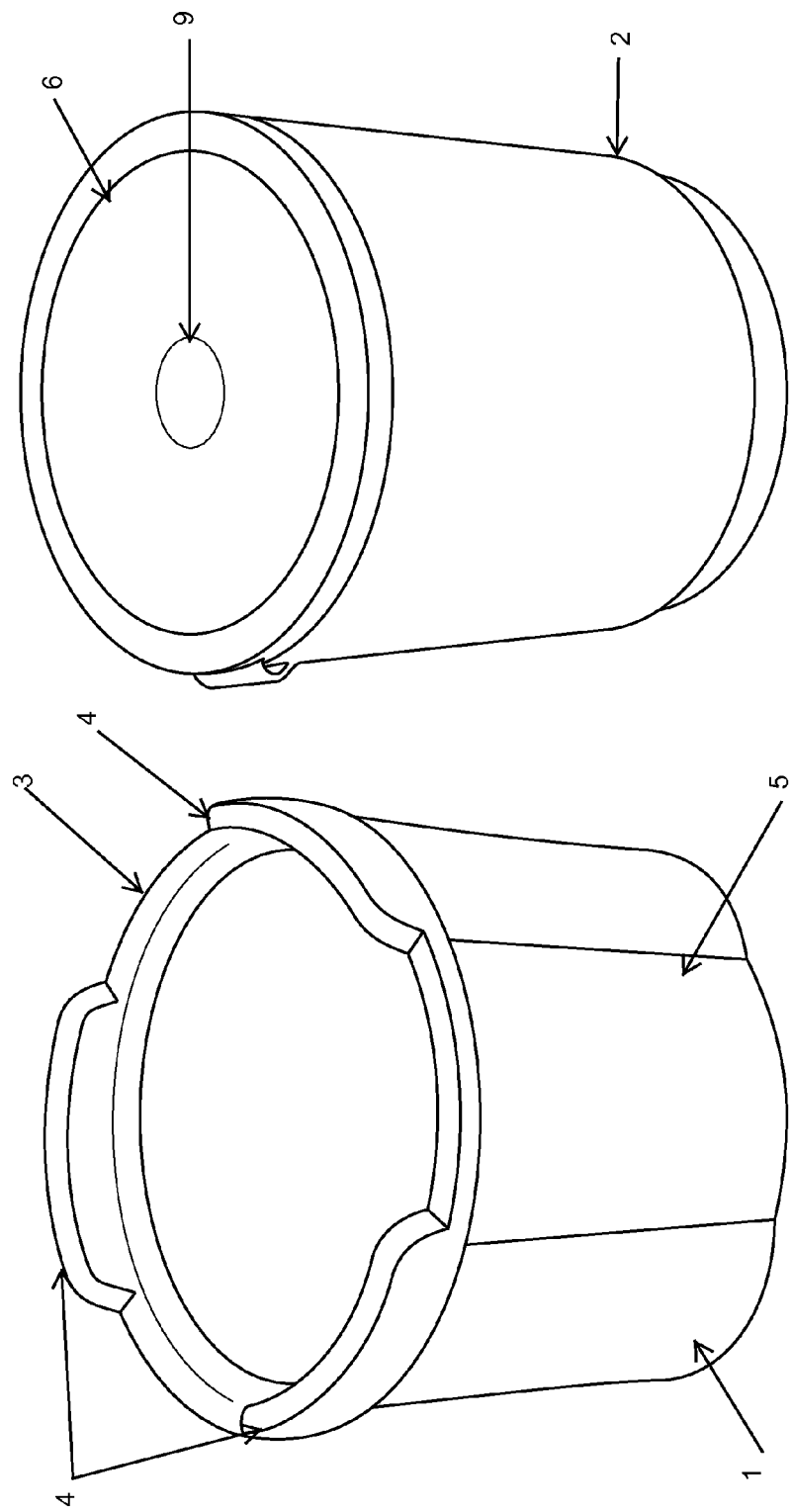

OXFORD STYLE SAMPLE CUP

FIELD OF THE INVENTION

This invention relates to the design and construction of a novel sample cup including integral venting cap for use in XRF Spectroscopy.

BACKGROUND OF THE INVENTION

The present invention describes a novel sample cup for use in XRF Spectroscopy.

Spectroscopic analysis (XRF Spectroscopy) utilizes sample cups to contain liquid or powder samples for elemental analysis. Sample cups generally have a thin transparent film bottom and may include a top end formed integral with the cup body known as a single ended design. Alternatively, the sample cup may include a second thin film or be secured at the top end, known as a double open end design. Sample cups are generally delivered to the analyst in parts comprised of a side wall member and complementary secondary member, which members are assembled in combination with a separate thin film component to construct a single sample cup. The sample cup, with its liquid or powder sample contained therein, is then manually transported to an XRF instrument and placed in a holder, thin film bottom down, for analysis.

In many instances, a liquid sample is deposited in a sample cup. A sample cup design utilizing a separate cap assembly to be manually applied to the sample cup body after deposit of the sample into the sample cup body requires manipulating the sample cup body, sample deposit via pipette and cap assembly. This creates handling problems and opportunities for contamination of the sample and contamination or damage to the thin film assembled to the bottom of the sample cup. The ability to reduce the number of manipulated items increases technician productivity and reduces the opportunities for contamination or damage to the sample cup and sample specimen.

In certain instances, provisions for venting may be necessary where a tested sample vents liquids or gases. Capped sample cups may contain a permanent vent hole to the outside atmosphere or a snap-off vent hole, also venting to the outside atmosphere. Venting is not always necessary or preferred particularly if the known sample is in the form of a loose powder; however and so a versatile sample cup capable of serving a venting or non-venting application constitutes a superior design.

In the case of violently venting liquids or gases, overflow chambers have been designed into sample cup designs to contain any venting liquids and prevent contamination or damage to the instrumentation. Existing design overflow chambers however, are limited by the sidewall and reservoir dimensions with a larger overflow chamber thereby reducing the sample reservoir capacity. Furthermore, liquid overflow displaced to existing design overflow chambers cannot be recycled or returned to the sample reservoir for testing. A superior design would provide for a larger overflow capacity without reducing the cross-sectional capacity of the sample reservoir, allow for return of vented liquids to the sample reservoir, and fully contain all liquids and gases within the capped and sealed sample cup.

The present invention addresses these concerns, being easily manipulated with one hand while providing superior venting options.

BRIEF DESCRIPTION OF THE DRAWINGS

FIGS. 1-6 are various views (perspective and elevation) of the Oxford style sample cup.

DETAILED DESCRIPTION OF THE INVENTION

Figures 3, 4:
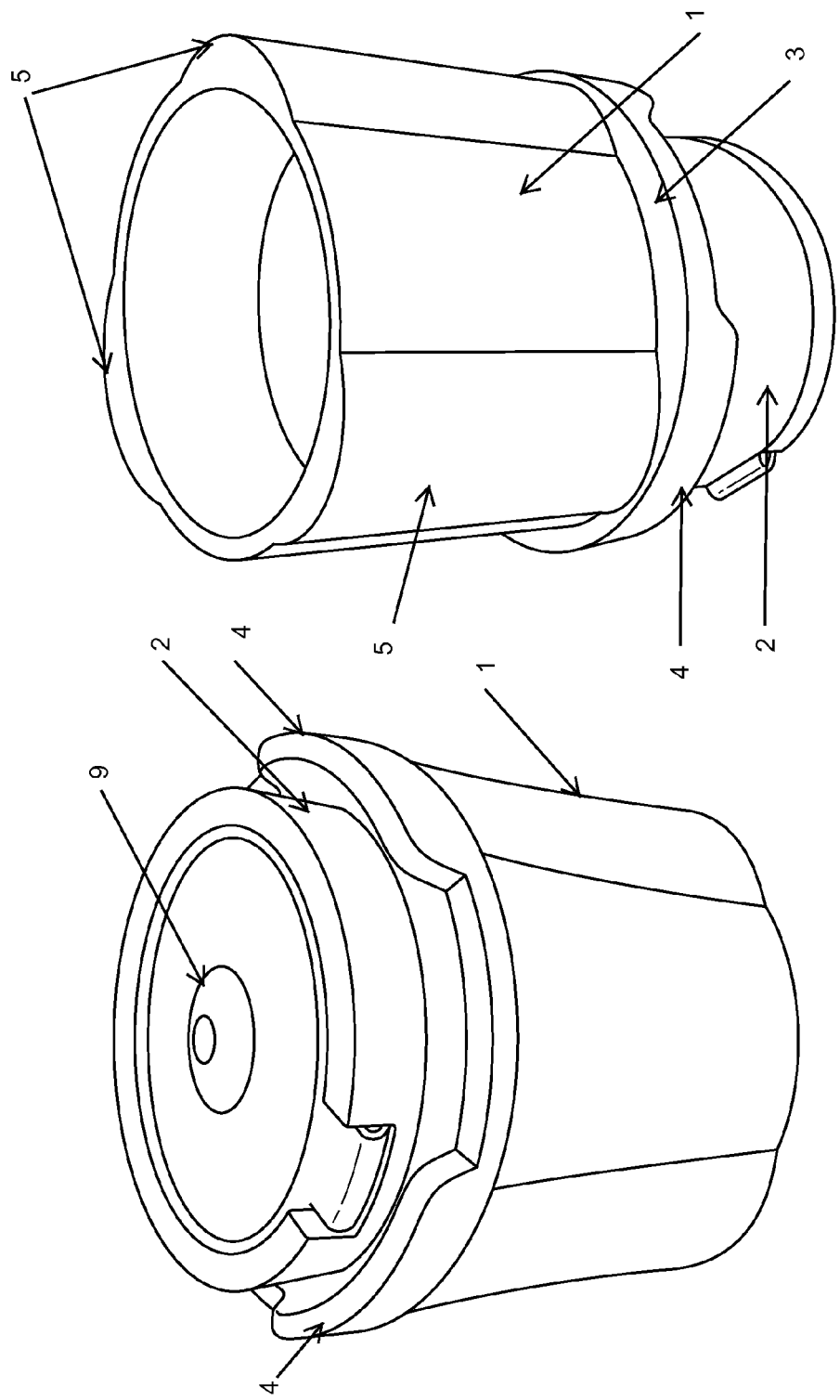

Shown in FIG. 1 is an outer member (1) with a top open end (shown) and a bottom open end (not shown). The outer member is dimensioned to frictionally fit circumferentially about inner member (2), shown in FIG. 2. Outer member is distinguished by a flanged upper rim (3), first projections (4) about the flanged upper rim, a lower body and second projections (5) about said lower body.

Shown in FIG. 2 is inner member (2) with a top closed end (not shown) and bottom open end. Inner member (2) is shown with a hinged cap (6) in the closed position. A center portion (9) is designed to be depressed to vent said inner top closed end.

Shown in FIG. 3 is the outer member (1) assembled in position over inner member (2).

Shown in FIG. 4 is outer member (1) partially assembled on inner member (2). In practice, a thin film would be placed between outer member (1) and inner member (2), the thin film dimensioned to cover the bottom open end of inner member (2) such that, upon assembly, a liquid sample would be retained for spectroscopic analysis. The first projections (4) may be dimensioned such that when the sample cup is assembled on a hard surface, such as a tabletop, the first projections will contact the tabletop when outer member is fully assembled over inner member. In at least one embodiment, this may result in approximately 0.005" clearance between the thin film covering the bottom open end of said inner member and a planar surface when the sample cup assembly is returned to an upright position, as illustrated in FIG. 3. Said flanged upper rim (3) and second projections (5) of outer member (1) may assist in gripping and manipulating the outer member during assembly and handling for testing.

Figure 5:
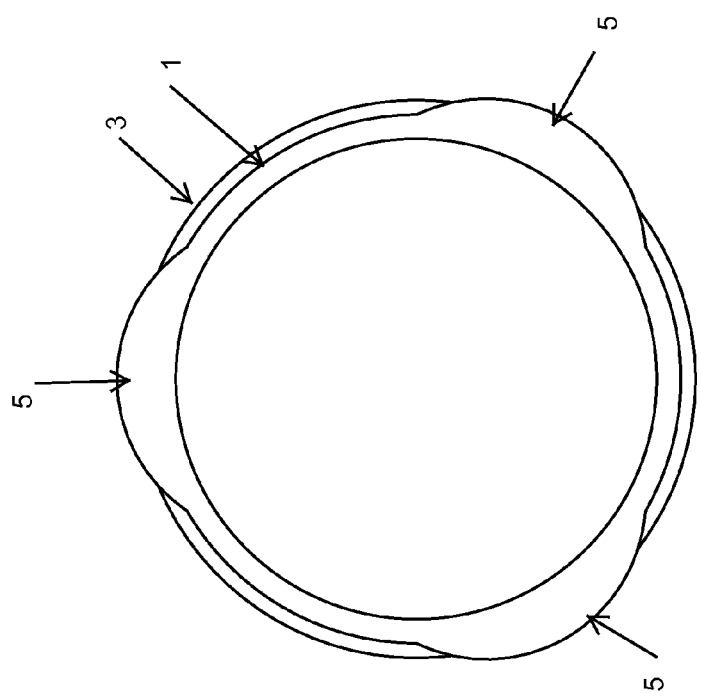

Shown in FIG. 5 is a bottom elevation view of outer member (1). Apparent in this view is the flanged upper rim (3), the lower body and second projections (5) about said lower body.

Figure 6:
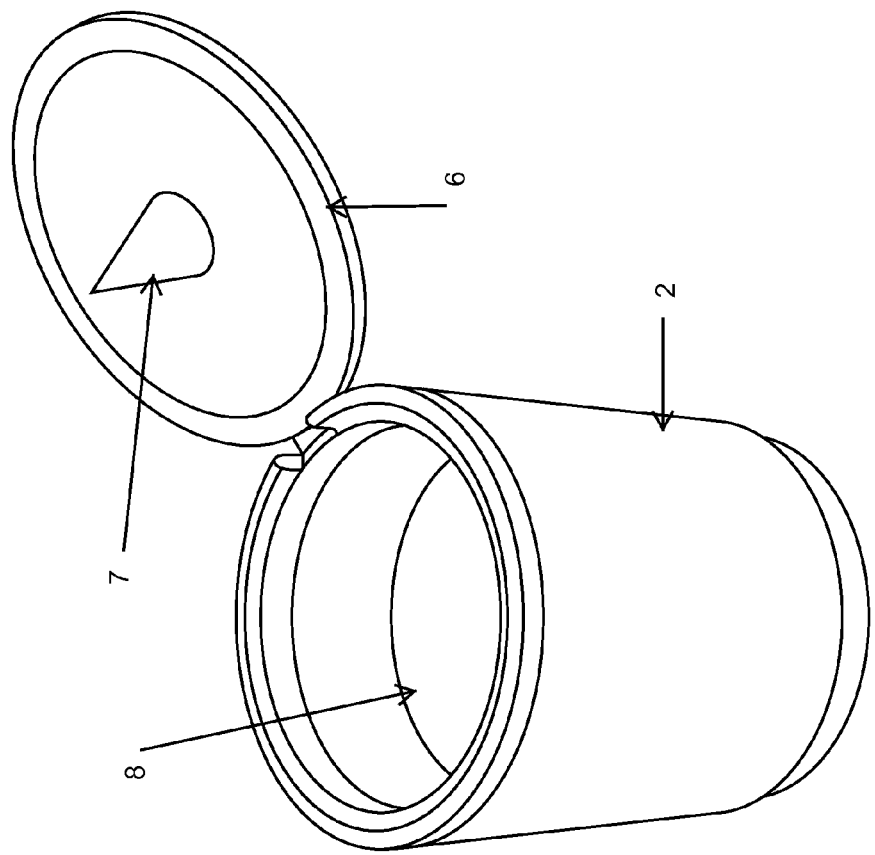

Shown in FIG. 6 is a perspective view of inner member (2) with hinged cap (6) in the open position. The top closed end (8) is shown disposed from the top wall edge of inner member (2), creating a space defined by the inner walls of inner member (2), top closed end (8) and hinged cap (6). This results in a dual chamber sample cup; the primary or testing chamber being defined by the inner walls of inner member (2), top closed end (8) and a thin film dimensioned to cover the previously bottom open end; and the secondary or venting chamber defined by the inner walls of inner member (2), top closed end (8) and hinged cap (6).

Protrusion (7) is dimensioned to allow hinged cap (6) to be placed in a closed position without piercing the top closed end (8) of inner member (2). In practice, when hinged cap (6) is in a closed position, a sample has been deposited and the sample cup has been fully assembled in preparation for testing, hinged cap (6) may be manually depressed thereby causing protrusion (7) to pierce the top closed end (8) to allow venting of liquids and gases into the space defined by the inner walls of inner member (2), top closed end (8) and hinged cap (6).

While the dimensions and shape of the sample cup components are not specifically defined and/or discussed herein, it is understood that such dimensions and shape may be adjusted or modified to meet industry needs or requirements without digressing from the spirit of the invention.

What is claimed:

1. A sample cup for retaining a sample to be analyzed spectrochemically, said sample cup comprising:
    an outer member comprising a top open end, a bottom open end, a flanged upper rim, first projections about said flanged upper rim, and second projections about the lower body of said outer member;
    an inner member comprising a top closed end disposed from a top wall edge of said inner member, a bottom open end and a hinged cap;
    wherein said outer member is dimensioned to frictionally fit circumferentially about said inner member; and
    wherein a thin-film of material is secured across said bottom open end of said inner member by application of said outer member to contain a liquid sample for spectrochemical analysis.

2. The sample cup according to claim 1, wherein said first projections are dimensioned to index against a hard planar surface to position a fully assembled outer member over said inner member such that there is about 0.005" clearance between the thin film covering the bottom open end of said inner member and a planar surface when the sample cup assembly is returned to an upright position.

3. The sample cup according to claim 1, wherein said inner member includes a protrusion situated on an inner surface of said cap to facilitate venting of the assembled sample cup when the top surface of said cap is depressed.

4. The sample cup according to claim 2, wherein said inner member includes a protrusion situated on an inner surface of said cap to facilitate venting of the assembled sample cup when the top surface of said cap is depressed.

5. The sample cup according to claim 1, wherein said second projections are semi elliptical.

6. The sample cup according to claim 1, wherein said second projections are squared.

7. The sample cup according to claim 2, wherein said second projections are semi elliptical.

8. The sample cup according to claim 2, wherein said second projections are squared.

* * * * *